United States Patent
Mine et al.

[11] Patent Number: 6,128,065
[45] Date of Patent: Oct. 3, 2000

[54] FERRIELECTRIC LIQUID CRYSTAL COMPOUND

[75] Inventors: Takakiyo Mine; Masahiro Johno; Tomoyuki Yui, all of Tsukuba, Japan

[73] Assignee: Mitsubishi Gas Chemical Company, Inc., Tokyo, Japan

[21] Appl. No.: 09/249,085

[22] Filed: Feb. 12, 1999

[30] Foreign Application Priority Data

Feb. 19, 1998 [JP] Japan ................... 10-037510

[51] Int. Cl.$^7$ .......... C09K 19/02; C09K 19/12; C07C 69/76
[52] U.S. Cl. ............. 349/182; 252/299.65; 560/65; 560/73
[58] Field of Search ............. 349/182; 560/65; 560/73; 252/299.65

[56] References Cited

U.S. PATENT DOCUMENTS

| | | | |
|---|---|---|---|
| 5,938,973 | 8/1999 | Motoyama et al. | 252/299.65 |
| 5,951,914 | 9/1999 | Matsumoto et al. | 252/299.67 |
| 5,955,001 | 9/1999 | Takigawa et al. | 252/299.66 |
| 5,968,413 | 10/1999 | Mine et al. | 252/299.65 |
| 5,980,780 | 11/1999 | Motoyama et al. | 252/299.64 |

FOREIGN PATENT DOCUMENTS

| | | |
|---|---|---|
| 0829468A | 3/1998 | European Pat. Off. . |
| 0853076A | 7/1998 | European Pat. Off. . |
| 0893429A | 1/1999 | European Pat. Off. . |
| 5-150257 | 6/1993 | Japan . |
| 5-249502 | 9/1993 | Japan . |
| 6-95080 | 8/1994 | Japan . |

OTHER PUBLICATIONS

Keiichi Nito et al, SID'94 Preprint, TFT–driven Monostable Ferroelectric Liquid Crystal Display with Wide Viewing Angle and Fast Response Times Molecular Orientational Structures in Ferroelectric, Ferrielectric and Antiferroelectric Smectic Liquid Crystal Phases as Studied by Conoscope Observation, JP Journal of Applied Physics, vol. 29, No. 1, pp L131–137,1990.

Physics and Electroinic Model of Deformed Helix Ferroelectric Liquid Crystal Displays, JP Journal of Applied Physics, vol. 33, pp 4950, 1994.

Reentrant Antiferroelectric Phase in 4–(1–Methylheptyloxycarbonyl)phenyl 4'–Octylbiphenyl–4–Carboxylate, JP, Jnl. of Applied Physics, vol. 31 793 1992.

C.J. Booth, et al., "The ferro–, ferri– and antiferro–electric properties of a series of novel 2– or 3–substituted–alkyl 4–(4'dodecyloxybiphenyl–4–carbonloxy)–benzoate esters", vol. 20., No. 6, pp. 815–823, Jun. 1, 1996.

Primary Examiner—C. H. Kelly
Attorney, Agent, or Firm—Sherman & Shalloway

[57] ABSTRACT

A ferrielectric liquid crystal compound of the general formula (1),

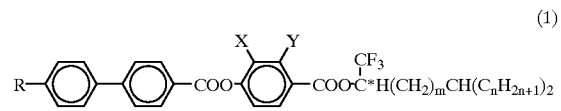

wherein R is a linear alkyl group having 6 to 12 carbon atoms, either each of X and Y is a hydrogen atom or one of X and Y is a hydrogen atom and the other is a fluorine atom, m is an integer of 1 to 2, n is 1 and C* is an asymmetric carbon. The above liquid crystal compound shows a ferrielectric phase in a wide temperature range and exhibits a fast response in spite of its small spontaneous polarization, and it is therefore remarkably useful for an active-matrix liquid crystal display device.

5 Claims, 1 Drawing Sheet

FERRIELECTRIC LIQUID CRYSTAL COMPOUND

FIELD OF THE INVENTION

The present invention relates to a novel ferrielectric liquid crystal compound suitable for use in an active-matrix type liquid crystal display device in which each pixel is individually driven.

PRIOR ART

A liquid crystal display device (LCD) as a flat panel display has been already superseding conventional Braun tube displays (CRT) mainly in the fields of portable machines and equipment. With the recent functional extension of personal computers and word processors and with the recent increase in the capacity of data processing, LCD is also required to have high functions such as a higher display capacity, full-color display, a wide viewing angle, a high-speed response and a higher contrast.

As a liquid crystal display method (liquid crystal driving method) to comply with the above requirements, there is proposed and practically used an active matrix (AM) display device which works by a method in which thin film transistors (TFT) or diodes (MIM) are formed such that one transistor or diode corresponds to one pixel on a display screen and a liquid crystal is driven for one pixel independently of another.

The above AM display method has problems in that it is difficult to decrease a cost due to a low yield and that it is difficult to form a large display screen. Due to a high image quality, however, the above display method is about to surpass an STN method which has been a conventional mainstream and is to about to overtake CRT.

Problems to be Solved by the Invention

However, the above AM display device has the following problems due to the use of a nematic liquid crystal compound as a liquid crystal material.

(1) A nematic liquid crystal compound is used for TN mode, and the response speed is generally slow (several 10 ms). In the display of video frames, no good picture quality can be obtained.

(2) Since displaying uses a twisted state (twist alignment) of liquid crystal molecules, the viewing angle is narrow. In the display with a gray scale in particular, the viewing angle is sharply narrowed. That is, the contrast ratio, the color, etc., change depending upon viewing angles in a display screen.

For overcoming the above problems, in recent years, there have been proposed AM panels which use a ferroelectric liquid crystal compound or an anti-ferroelectric liquid crystal compound in place of the TN liquid crystal (Japanese Laid-open Patent Publications Nos. JP-A-5-249502, JP-A-5-150257 and JP-A-6-95080). However, the following problems remain to solve for the practical use of these liquid crystal compounds.

(3) A ferroelectric liquid crystal has spontaneous polarization. A picture sticking is liable to take place due to constant spontaneous polarization, and the driving is made difficult. In the display with a ferroelectric liquid crystal compound in a surface-stabilized mode, it is very difficult to perform a gray-scale display since only black and white is possible to be displayed in principle. For the gray-scale display, a special devising is required (e.g., ferroelectric liquid crystal device using monostability; Keiichi NITO et al., SID '94, Preprint, p. 48), and it is required to develop a very high technique for practical use.

(4) An anti-ferroelectric liquid crystal compound is free of the picture sticking problem described in the above (3) since it has no permanent spontaneous polarization.

However, the AM driving at least requires a liquid crystal material which can be driven at 10 V or less. However, the anti-ferroelectric liquid crystal generally has a high threshold voltage, and its driving at a low voltage is therefore difficult. Further, it has another problem that the gray-scale display is difficult since its optical response involves a hysteresis.

It is an object of the present invention to provide a novel material which can overcome the above problems and is suitable for use with AM driving. A liquid crystal compound having a ferrielectric phase is thinkable as the above novel material.

A ferrielectric liquid crystal compound having a ferrielectric phase (SCγ* phase) was found for the first time in 4-(1-methylheptyloxycarbonyl)phenyl-4-(4'-octyloxybiphenyl)carboxylate (called "MHPOBC" for short) in 1989 (Japanese Journal of Applied Physics, Vol. 29, No. 1, pp. L131–137 (1990)).

The structural formula and phase transition temperatures (° C.) of the MHPOBC are as follows.

Structure formula:

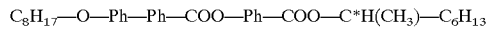

$C_8H_{17}$—O—Ph—Ph—COO—Ph—COO—C*H(CH$_3$)—C$_6$H$_{13}$ wherein Ph is a 1,4-phenylene group and C* is an asymmetric carbon atom.

Phase sequence:

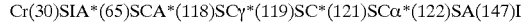

Cr(30)SIA*(65)SCA*(118)SCγ*(119)SC*(121)SCα*(122)SA(147)I wherein and Cr is a crystal phase, SIA* is a chiral smectic IA phase, SCA* is a chiral smectic CA phase (anti-ferroelectric phase), SCγ* is a chiral smectic Cγ phase (ferrielectric phase), SC* is a chiral smectic C phase (ferroelectric phase), SCα* is a chiral smectic Cα phase, SA is a smectic A phase, and I is an isotropic phase.

BRIEF DESCRIPTION OF DRAWINGS

For explaining a ferrielectric phase, FIG. 1 shows molecular arrangement states of a ferrielectric phase, and FIG. 2 shows an optical response of a ferrielectric phase to a triangular wave.

Figure 1:
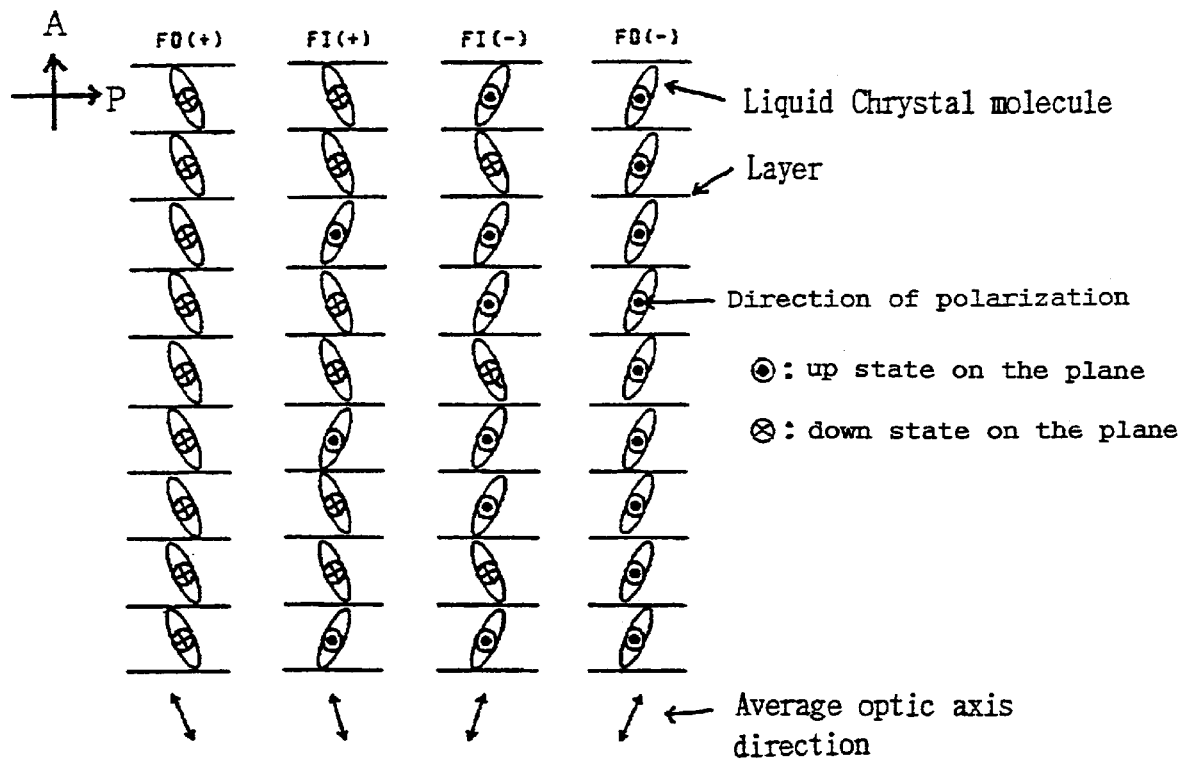
FIG. 1 shows a molecular arrangement of a ferrielectric phase. FI(+) and FI(−) show a ferrielectric state, and FO(+) and FO(−) show a ferroelectric state.

A ferrielectric phase has a molecular arrangement state of FI(+) (a case where an applied voltage is positive) or a molecular arrangement state of FI(−) (case where an applied voltage is negative) as shown in FIG. 1. In a state free of an electric field, FI(+) and FI(−) are equivalent and are therefore co-present.

In a state free of an electric field, therefore, average optical axes are in the direction of a layer normal, and the state free of an electric field is in a dark state under the condition of a polarizer shown in FIG. 1. This state corresponds to a portion showing a transmitted light intensity of 0 at an applied voltage of 0 in FIG. 2.

Further, each of FI(+) and FI(−) has spontaneous polarization as is clearly shown by the molecular arrangement states, while the spontaneous polarizations are offset in a state in which these are co-present. As a result, an average spontaneous polarization is zero. This shows that, like an anti-ferroelectric phase, a ferrielectric phase is free from a picture sticking phenomenon found in a ferroelectric phase.

When a voltage applied to a ferrielectric phase is increased, a region (domain) having an extinction position appears at a voltage lower than a voltage at which a ferroelectric state is reached. This shows that the above domain has an optical axis in the direction which tilts from the direction of layer normal although the tilt is not so large as that in a ferroelectric state.

Figure 2:
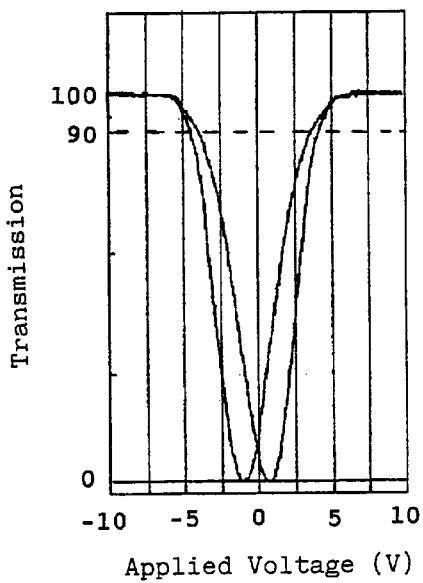
FIG. 2 shows an optical response of a ferrielectric phase to a triangular wave voltage.

The above intermediate state is considered FI(+) or FI(−). In this case, not a continuous change in the transmission but a stepwise change in the transmission ought to be observed between voltages of 0 V and 4 V in FIG. 2. In FIG. 2, however, a continuous change in the transmission is observed. It is assumed that the above occurs because the threshold voltage in FI(+)→FO(+) or FI(−)→FO(−) is not sharp.

In the present invention, a liquid crystal phase which necessarily shows the above-explained intermediate state is called a ferrielectric phase, and a liquid crystal compound of which the ferrielectric phase is the broadest in the phase sequence is called a ferrielectric liquid crystal compound.

When the applied voltage is further increased, the ferrielectric phase undergoes a phase transition to a stable ferroelectric phase FO(+) or FO(−) depending upon a direction of the electric field. That is, a portion in which the transmission is brought into a saturated state (flat portions on left and right sides) in FIG. 2 is FO(+) or FO(−).

In the above ferroelectric state FO(+) or FO(−), there is exhibited a spontaneous polarization greater than that in the ferrielectric state FI(+) or FI(−) as is seen in FIG. 1.

As described above, the ferrielectric phase permits the use of a co-presence state of FI(+) and FI(−) as a dark state and the use of ferroelectric states of FO(+) and FO(−) as a light state.

A conventional ferroelectric phase provides a switching between FO(+) and FO(−), while the ferrielectric phase has a great characteristic feature in switching among four states of FO(+), FI(+), FI(−) and FO(−).

As the display principle uses switching in the plane of display screen, the display device having a decreased viewing angle dependency can be realized.

As shown in FIG. 2, generally, a ferrielectric phase highly tends to show a small difference between the voltage at which it changes from a ferrielectric state to a ferroelectric state and the voltage at which it changes from a ferroelectric state to a ferrielectric state, that is, the width of its hysteresis strongly tends to be very small. It characteristically shows a V-letter-shaped optical response and therefore has properties suitable for use for active matrix driving AM driving and the display with a gray scale in AM driving.

Further, in the phase change of the ferrielectric phase on the basis of a voltage, the applied voltage (phase transition voltage) required for a change from a ferrielectric state to a ferroelectric state tends to be very small as compared with that of an anti-ferroelectric phase, and it can be therefore said that the ferrielectric phase is suitable for AM driving.

However, the number of ferrielectric liquid crystal compounds that have been synthesized so far is very few, and when the application to an AM driving device is taken into account, few ferrielectric liquid crystal compounds that have been already known are satisfactory in respect of hysteresis and a phase transition voltage.

In the active matrix driving device, further, it is an essential problem in practice how large or small the spontaneous polarization of the ferrielectric liquid crystal compound is.

J. Funfscilling et al show that the degree of the voltage required for driving a liquid crystal having spontaneous polarization is in proportion to the spontaneous polarization (Jpn. J. Appl. Phy. Vol. 33 pp. 4950 (1994)). It is desirable from the aspect of driving voltage that the spontaneous polarization is as small as possible.

On the other hand, it is said that the response speed in the phase transition from a ferrielectric state to a ferroelectric state is largely in proportion to the degree of spontaneous polarization.

It is therefore practically very advantageous if there can be provided a ferrielectric liquid crystal compound having a small spontaneous polarization and having a high response speed.

Means to Solve the Problems

According to the present invention, there is provided a ferrielectric liquid crystal compound of the general formula (1),

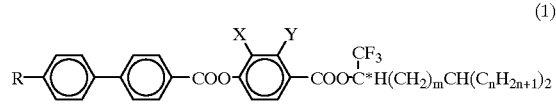

wherein R is a linear alkyl group having 6 to 12 carbon atoms, either each of X and Y is a hydrogen atom or one of X and Y is a hydrogen atom and the other is a fluorine atom, m is an integer of 1 to 2, n is 1 and C* is an asymmetric carbon.

In the compound of the general formula (1), provided by the present invention, R is a linear alkyl group having 6 to 12 carbon atoms, preferably a linear alkyl group having 8 to 10 carbon atoms. m is an integer of 1 to 2, preferably of 2. Particularly preferred is a compound of the general formula (1) in which m is 2. Either each of X and Y is a hydrogen atom, or one of X and Y is a hydrogen atom and the other is a fluorine atom. Preferred is a compound of the general formula (1) in which X is a hydrogen atom and Y is a fluorine atom.

In the ferrielectric liquid crystal compound of the general formula (1) in the present invention, the transition temperature from a high temperature side to a ferrielectric phase is preferably at least 40° C. The voltage at which the phase transition takes place from a ferrielectric state to a ferroelectric state is in proportion to a driving voltage, and it is therefore 5 V/μm or less, preferably 3 V/μm or less, in view of the voltage resistance degree of currently used driving ICs.

Preferably, further, the voltage (phase transition voltage I) at which the phase transition takes place from a ferrielectric state to a ferroelectric state and the voltage (phase transition voltage II) at which the phase transition takes place from a ferroelectric state to a ferrielectric state have a smaller difference.

At least one of the ferrielectric liquid crystal compound of the present invention is suitable as a base liquid crystal compound for a ferrielectric liquid crystal composition or as a compound for modifying a ferrielectric liquid crystal composition. The above ferrielectric liquid crystal composition can form an active matrix liquid crystal display device by being placed between substrates on which non-linear active elements such as thin film transistors or diodes are provided for each pixels.

An optically active alcohol used for the synthesis of the compound of the present invention can be easily produced by the method which the present inventors have already published.

The method of the production thereof, for example, when m is 2 and n is 1, is outlined as follows.

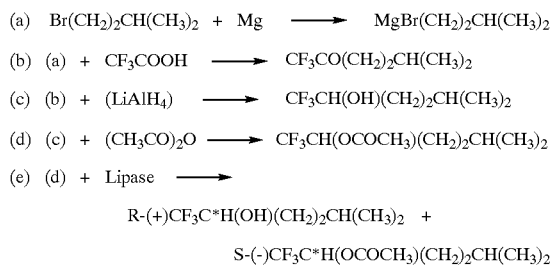

The above reactions will be briefly explained as follows.

(a) shows the preparation of a Grignard reagent.

(b) shows a carbon-propagation reaction between the Grignard reagent and a trifluoroacetic acid.

(c) shows a reduction reaction of a ketone.

(d) shows the acetylation of a racemic alcohol with an anhydrous acetic acid.

(e) shows the asymmetric hydrolysis of an acetate with lipase (e.g., lipase MY). This reaction gives an intended R-configuration optically active alcohol and an S-configuration acetate. The S-configuration acetate is hydrolyzed to give a S-configuration optically active alcohol.

EXAMPLES

The present invention will be more specifically explained with reference to Examples hereinafter, while the present invention shall not be limited thereto.

Example 1

(General formula (1) wherein $R=C_{10}H_{21}$, X=H, Y=F, m=2 and n=1)

Preparation of R-(+)-3-fluoro-4-(1-trifluoromethyl-4-methyl-pentyloxycarbonyl)phenyl-4'-n-decylbiphenyl-4-carboxylate (1) Preparation of 4-acetoxy-2-fluorobenzoic acid 4.3 Grams of 4-hydroxy-2-fluorobenzoic acid and 8.4 g of anhydrous acetic acid were placed in a two-necked flask and mixed, and five drops of sulfuric acid was added with cooling with water. After heat generation terminated, the mixture was heated at 80° C. for 30 minutes. Then, the reaction mixture was discharged into cold water, and a precipitated crystal was recovered by filtration.

The crystal was dried under vacuum and used in a subsequent step. The yield of the acid was 4.7 g.

(2) Preparation of R-(+)-4-acetoxy-2-fluoro-1-(1-trifluoromethyl-4-methyl-pentyloxycarbonyl)benzene 1.0 Gram of 4-acetoxy-2-fluorobenzoic acid was added to 7 ml of thionyl chloride, and the mixture was allowed to react under reflux for 5 hours. Then, excess thionyl chloride was distilled off, and then, a mixture containing 1 ml of pyridine, 4 ml of dry ether and 0.6 g of R-(+)-1,1,1-trifluoro-2-hydroxy-5-methyl-hexane was dropwise added. The resultant mixture was stirred at room temperature for 1 day and then diluted with 200 ml of ether, and an organic layer was washed consecutively with diluted hydrochloric acid, with a 1N sodium hydroxide aqueous solution and with water and dried over magnesium sulfate.

The solvent was distilled off to obtain a crude end product, and the crude end product was purified by silica gel column chromatography using hexane/ethyl acetate as a solvent, to give 1.1 g of the end product.

(3) Preparation of R-(+)-4-hydroxy-2-fluoro-1-(1-trifluoromethyl-4-methyl-pentyloxycarbonyl)benzene 1.0 Gram of the compound obtained in the above (2) was dissolved in 30 ml of ethanol, and 3 g of benzylamine was dropwise added. Further, the mixture was stirred at room temperature for 1 day and then diluted with 300 ml of ether, and the resultant mixture was washed consecutively with diluted hydrochloric acid and water and dried over magnesium sulfate.

The solvent was distilled off, followed by isolation and purification by silica gel column chromatography, to give 0.5 g of the end product.

(4) Preparation of R-(+)-3-fluoro-4-(1-trifluoromethyl-4-methyl-pentyloxycarbonyl)phenyl-4'-n-decyloxybiphenyl-4-carboxylate To 1.0 g of commercially available 4'-n-decylbiphenyl-4-carboxylic acid was added 10 ml of thionyl chloride, and the mixture was refluxed under heat for 10 hours. Excess thionyl chloride was distilled off, and then 10 ml of pyridine and 25 ml of toluene were added. Then, 25 ml of a benzene solution containing 0.5 g of the compound obtained in the above (3) was dropwise added, and the mixture was allowed to react at room temperature for 10 hours.

After completion of the reaction, the reaction mixture was diluted with 300 ml of ether and washed consecutively with diluted hydrochloric acid, with a 1N sodium carbonate aqueous solution and with water, and an organic layer was dried over magnesium sulfate. Then, the solvent was distilled off, followed by isolation by silica gel column chromatography and recrystallization from ethanol, to give 0.7 g of the intended product.

The following formula shows the structure of the intended product obtained in Example 1, and Table 1 shows $^1$H-NMR spectral data of the intended product.

The spontaneous polarization was determined by applying a triangular wave voltage of 10 V at 50° C. and measuring a polarization inversion voltage.

Further, the response speed was defined to be a time required for a change from 0% to 90% in the light transmittance by applying a rectangular wave voltage of 8 V and 10 Hz.

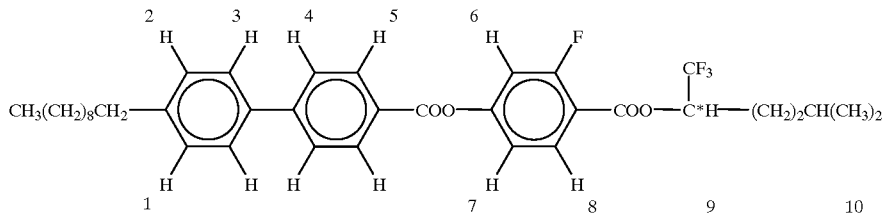

TABLE 1

| Hydrogen atom number | 1 | 2 | 3 | 4 | 5 | 6 | 7 | 8 | 9 | 10 |
|---|---|---|---|---|---|---|---|---|---|---|
| Example 1 (δ (ppm)) | 2.6 | 7.3 | 7.6 | 7.8 | 8.2 | 7.2 | 7.2 | 8.1 | 5.5 | 0.9 |

The liquid crystal phases of the obtained compound as the intended product were identified as follows, and Table 2 shows the results. The compound was identified for liquid crystal phases by texture observation, conoscopic figure observation and DSC (differential scanning calorimeter) measurement. The observation of a conoscopic figure is effective means for identifying a ferrielectric phase. The conoscopic figure observation was conducted according to a literature (J. Appl. Phys. 31, 793 (1992)).

Then, the ferrielectric liquid crystal compound obtained in Example 1 was measured for an optical response, and Table 2 shows the result. A cell was prepared by the following procedures.

A pair of glass plates with insulating film ($SiO_2$, thickness; 50 nm) and ITO electrodes were coated with polyimide (thickness; about 80 nm), and one of the glass plates was rubbed.

A pair of the glass plates were attached to each other through a spacer having a particle diameter of 1.6 μm to form a test cell. The cell had a thickness of 2 μm.

The liquid crystal compound was heated until it showed an isotropic phase, and the compound was charged into the test cell by capillarity. Then, the cell was gradually cooled at a rate of 1° C./minute to align the liquid crystal in parallel.

The light transmittance was defined as follows. A lowest transmission was 0% of light transmittance, and a highest transmission was 100% of light transmittance. The phase transfer voltage was defined to be a voltage found at a light transmittance of 90%.

A triangular wave voltage of ±10 V and 5 Hz was applied to the test cell, and a voltage (phase transition voltage I) in the transition from a ferrielectric phase to a ferroelectric phase and a voltage (phase transition voltage II) in the transition from a ferroelectric phase to a ferrielectric phase were determined at 50° C.

TABLE 2

| | Phase sequence | Phase transition voltage | Response time | Spontaneous polarization |
|---|---|---|---|---|
| Example 1 | I(64)SCγ*(36)Cr | 0.9 V/μm | 30 μsecond | 144 $_n$C/cm$^2$ |

In Table 2, parenthesized values show transition temperature (° C.) in the process of decreasing a temperature, I stands for an isotropic phase, SCγ* stands for a ferrielectric phase, and Cr stands for a crystal phase.

Example 2

(General formula (1) wherein R=$C_8H_{17}$, X=H, Y=F, m=2 and n=1)

Preparation of R-(+)-3-fluoro-4-(1-trifluoromethyl-4-methyl-pentyloxycarbonyl)4'-n-octylbiphenyl-4-carboxylate End products were prepared in the same manner as in Example 1 except for the use of 4'-n-octylbiphenyl-4-carboxylate which was replaced with 4'-n-decylbiphenyl-4-carboxylate in Example 1.

Table 3 shows $^1$H-NMR spectral data.

Further, values of physical properties were determined in the same manner as in Example 1. The results are shown in Table 4.

Comparative Example 1

(General formula (1) wherein R=$C_{10}H_{21}$, X=H, Y=F, m=3 and n=1)

Preparation of R-(+)-3-fluoro-4-(1-trifluoromethyl-5-methyl-hexyloxycarbonyl)4'-n-decylbiphenyl-4-carboxylate End products were prepared in the same manner as in Example 1 except for the use of R-(+)-1,1,1-trifluoro-2-hydroxy-6-methyl-heptane which was replaced with R-(+)-1,1,1-trifluoro-2-hydroxy-5-methyl-hexane in Example 1.

Table 3 shows $^1$H-NMR spectral data.

Further, values of physical properties were determined in the same manner as in Example 1. The results are shown in Table 4. It is obvious from Table 4 that the determining of values of physical properties is difficult as the range of a ferrielectric phase is remarkably narrow.

Comparative Example 2

(General formula (1) wherein R=$C_9H_{19}$, X=H, Y=F, M=1 and n=2)

Preparation of R-(+)-3-fluoro-4-(1-trifluoromethyl-3-ethyl-pentyloxycarbonyl)4'-n-nonylbiphenyl-4-carboxylate End products were prepared in the same manner as in Example 1 except for the use of 4'-n-nonylbiphenyl-4-carboxylate and R-(+)-1,1,1-trifluoro-2-hydroxy-4-ethyl-hexane which were replaced with 4'-n-decylbiphenyl-4-carboxylate and R-(+)-1,1,1-trifluoro-2-hydroxy-5-methyl-hexane in Example 1.

Table 3 shows $^1$H-NMR spectral data.

Further, values of physical properties were determined in the same manner as in Example 1. The results are shown in Table 4. This compound has an anti-ferroelectric phase without having a ferrielectric phase.

TABLE 3

| Hydrogen atom number | 1 | 2 | 3 | 4 | 5 | 6 | 7 | 8 | 9 |
|---|---|---|---|---|---|---|---|---|---|
| Example 2 (δ (ppm)) | 2.6 | 7.3 | 7.8 | 7.6 | 8.3 | 7.2 | 7.1 | 8.0 | 5.5 |
| Comparative Example 1 (δ (ppm)) | 2.6 | 7.3 | 7.8 | 7.6 | 8.3 | 7.2 | 7.1 | 8.0 | 5.5 |
| Comparative Example 2 (δ (ppm)) | 2.6 | 7.3 | 7.8 | 7.6 | 8.3 | 7.2 | 7.1 | 8.0 | 5.6 |

TABLE 4

| | Phase sequence | Phase transition voltage | Spontaneous polarization |
|---|---|---|---|
| Example 2 | I(76)SCγ*(<10)Cr | 2.3 V/μm | 182 nC/cm$^2$ |
| Comparative Example 1 | I(55)SCγ*(53)Cr | | |

TABLE 4-continued

| | Phase sequence | Phase transition voltage | Spontaneous polarization |
|---|---|---|---|
| Comparative Example 2 | I(53)SCA*(51)Cr | | |

Effect of the Invention

The novel ferrielectric liquid crystal compound provided by the present invention shows a ferrielectric phase in a broad temperature range and exhibits a fast response in spite of its small spontaneous polarization, and it is remarkably useful as a practical material.

What is claimed is:

1. A ferrielectric liquid crystal compound of the general formula (1),

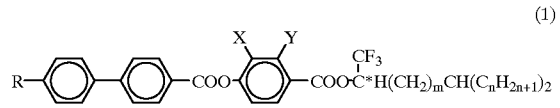

(1)

wherein R is a linear alkyl group having 6 to 12 carbon atoms, either each of X and Y is a hydrogen atom or one of X and Y is a hydrogen atom and the other is a fluorine atom, m is an integer of 1 to 2, n is 1 and C* is an asymmetric carbon.

2. The ferrielectric liquid crystal compound of claim 1, which has the general formula (1) in which R is a linear alkyl group having 8 to 10 carbon atoms.

3. The ferrielectric liquid crystal compound of claim 1, which has the general formula (1) in which m is 2.

4. The ferrielectric liquid crystal compound of claim 1, which has the general formula (1) in which X is a hydrogen atom and Y is a fluorine atom.

5. An active-matrix liquid crystal display device comprising the ferrielectric liquid crystal compound of claim 1, which is interposed between substrates on which non-linear active elements of thin film transistors or diodes are provided for individual pixels.

* * * * *